United States Patent
Homedes-Beguer et al.

(10) Patent No.: US 11,154,536 B2
(45) Date of Patent: Oct. 26, 2021

(54) PYRAZOLINE-DERIVED COMPOUND AND ITS USE IN A WEEKLY DOSAGE REGIME AGAINST INFLAMMATION AND PAIN DERIVED FROM DEGENERATIVE JOINT DISEASE IN MAMMALS

(71) Applicant: ECUPHAR N.V., Oostkamp (BE)

(72) Inventors: Josep Homedes-Beguer, Barcelona (ES); David Sabate-Elias, Barcelona (ES)

(73) Assignee: ECUPHAR N.V., Barcelona (ES)

( * ) Notice: Subject to any disclaimer, the term of this patent is extended or adjusted under 35 U.S.C. 154(b) by 413 days.

(21) Appl. No.: 15/518,871

(22) PCT Filed: Oct. 13, 2015

(86) PCT No.: PCT/EP2015/073635
§ 371 (c)(1),
(2) Date: Apr. 13, 2017

(87) PCT Pub. No.: WO2016/059028
PCT Pub. Date: Apr. 21, 2016

(65) Prior Publication Data
US 2017/0231961 A1  Aug. 17, 2017

(30) Foreign Application Priority Data
Oct. 16, 2014 (EP) ..................................... 14382396

(51) Int. Cl.
*A61K 31/415* (2006.01)
(52) U.S. Cl.
CPC ................................. *A61K 31/415* (2013.01)
(58) Field of Classification Search
None
See application file for complete search history.

(56) References Cited

FOREIGN PATENT DOCUMENTS

EP  1 083 171 B1  3/2001
ES  WO9962884  * 12/1999 ........... C07D 231/06

OTHER PUBLICATIONS

Sinusas, K., Osteoarthritis: Diagnosis and Treatement, 2012, Am Fam Physician, 85(1), pp. 49-56 (Year: 2012).*
Sahin et al., The Operational Multiple Dosing Half-life: A key to Defining Drug Accumulation in Patients and to Designing Extended Release Dosage Forms, 2008, Pharm Res, 25(12), pp. 2869-2877 (Year: 2008).*
International Search Report corresponding to International Application No. PCT/EP2015/073635 dated Jul. 1, 2016.
Cox et al. (2010) The pharmacokinetics of mavacoxib, a long-acting COX-2 inhibitor, in young adult laboratory dogs. Journal of Veterinary Pharmacology and Therapeutics 33(5):461-470.
International Preliminary Report on Patentability corresponding to International Application No. PCT/EP2015/073635 dated Apr. 8, 2017.
Office Action corresponding to European Patent Application No. 14382396.1 dated Mar. 19, 2015.
Reinoso et al. (2001) Pharmacokinetics of E-6087, a new anti-inflammatory agent, in rats and dogs. Biopharmaceutics & Drug Disposition 22(6):231-242.
Toutain et al. (2001) A pharmacokinetic/pharmacodynamic approach vs. a dose titration for the determination of a dosage regimen: the case of nimesulide. a Cox-2 selective nonsteroidal anti-inflammatory drug in the dog. Journal of Veterinary Pharmacology and Therapeutics 24(1):43-45.

* cited by examiner

*Primary Examiner* — Savitha M Rao
*Assistant Examiner* — Gregg Polansky
(74) *Attorney, Agent, or Firm* — Jenkins, Wilson, Taylor & Hunt, P.A.

(57) ABSTRACT

The present invention refers to the use of the compounds E-6087 in a weekly dosage regime for the treatment of pain and inflammation associated to a degenerative joint disease such as osteoarthritis or a condition associated to any such disease such as lameness. The present invention is directed to the treatment of mammals, preferably of dogs.

8 Claims, 9 Drawing Sheets

PYRAZOLINE-DERIVED COMPOUND AND ITS USE IN A WEEKLY DOSAGE REGIME AGAINST INFLAMMATION AND PAIN DERIVED FROM DEGENERATIVE JOINT DISEASE IN MAMMALS

FIELD OF THE INVENTION

The present invention relates to the use of a pyrazoline derived compound in a particular dosage regime for the treatment of pain and inflammation associated to a degenerative joint disease or condition in mammals. In particular, the invention refers to the selectively COX-2 blocking compound E-6087 for use in a weekly dosage regime for the treatment of pain and inflammation associated to a degenerative joint disease such as osteoarthritis or a condition associated to any such disease such as lameness. The present invention is directed to the treatment of mammals, preferably of dogs.

BACKGROUND OF THE INVENTION

Degenerative joint disease, also referred to as canine osteoarthritis, or osteoarthrosis, is a disease process characterized by pain and lameness associated with pathological changes in the tissues of synovial joints, including the loss of articular cartilage (Sanderson, R. O., Beata, C., Flipo, R. M., Genevois, J. P., Macias, C. Tacke, S., Vezzoni, A and Innes, J F (2009). Systematic review of the management of canine osteoarthritis. The Veterinary Record, 164:418-424. and Innes, J., O'Neil, T. and Lascelles, D. (2010) Use of non-steroidal anti-inflammatory drugs for the treatment of canine osteoarthritis. In Practice, 32: 126-137). Specifically, there is an increased degradation of the extracellular matrix of the articular cartilage, with subsequent production of inflammatory mediators and degenerative enzymes that lead to further degenerative and inflammatory changes.

There is not a known cure for degenerative joint disease. Its management usually consists in combinations of therapy like non-steroidal anti-inflammatory drugs (NSAIDs) and analgesics, nutraceuticals, functional foods, physical therapy and alternative therapies such as acupuncture.

NSAIDs are acidic anti-inflammatory agents that inhibit the enzyme cyclooxygenase (COX) which catalyses the conversion of arachidonic acid to prostaglandins and thromboxane. Advances in the early 1990s showed the presence of two isoforms of COX, namely COX-1 and COX-2.

On the one hand, COX-1 is considered to be the constitutive form as it produces prostaglandins that are important for normal physiological function and are produced by many tissues, including gastrointestinal cells, platelets, endothelial cells and renal cells. On the other hand, COX-2 is considered to be an inducible form of the enzyme, the expression of which is tightly controlled under basal conditions but is dramatically up regulated in the presence of inflammation. Proinflammatory cytokines are known to stimulate the expression of COX-2 in many cells, including synovial cells, endothelial cells, chondrocytes, osteoblasts, monocytes and macrophages. Indeed, synovial and subchondral bone tissue from hips of dogs with osteoarthritis have been shown to present increased COX-2 expression compared with healthy dogs.

The main mechanism of action of most NSAID's is the blocking of prostaglandin synthesis by non-selectively binding to and inhibiting the action of the COX-1 and COX-2 isoenzymes. The major therapeutic and toxic effects of NSAIDs are associated with this mechanism, specially when long treatments are required, like in degenerative joint disease.

During the last decades, a new class of NSAID's, the Coxibs, has been developed, the action of which is highly selective against the isoenzyme COX-2, this allowing the aimed therapeutic effects without the common side effects related to COX-1 inhibition. Firocoxib (Previcox®), Mavacoxib (Trocoxil®), Robenacoxib (Onsior®) and Cimicoxib (Cimalgex®) are the currently licensed Coxibs in Europe and/or the USA for management of degenerative joint disease in dogs.

There are currently two kinds of coxibs on the market which are subject to a different dosage regime: the ones that are administered daily (Previcox®, Onsior®, Cimalgex®) and those that are administered once-monthly (Trocoxil®).

The treatment of inflammatory joint disease in mammals and in particular in pets like dogs has been carried out traditionally with the daily oral administration of coxibs. The oral administration of medicaments in animals and pets contrary to the case of human has mainly two problems. The first is the acceptance of the medication by the animal which can vary from a good acceptance to low acceptance. To solve this problem, formulations with aroma have been developed in order to increase the animal appetite and facilitate the oral intake. The second problem is that a daily dosage is subjected to a very close supervision of the treatment by the person administering the medicament to the animal or pet. It is usual that owner of pets misses the administration of some doses either because an oversight or because it is complicated to have contact with the animal everyday. These problems are even more important for long or chronic treatments such as osteoarthritis where loss of adherence to the treatment to the dosage regime may result in lack of efficacy or incomplete efficacy.

In order to solve this problem, it was proposed and developed a product for a monthly treatment which in principle is suitable for safeguarding adherence to treatment in long treatments. However the administration of a medicament that is going to be present in the animal organism for a month, limits the administration of other medicaments that the animals may need during treatment. The impossibility of removing the product for such a long period is also a risk for those animal that may develop an adverse reaction to the product, therefore security of the treatment with a monthly product is a matter of concern by the veterinarian prescripting such treatment.

Thus here is a need to develop a treatment that avoids the disadvantage of administering a daily dosage to the animal in order to improve the adherence to the treatment, but at the same time avoids the administration of a monthly dosage that leads to blood levels of the anti-inflammatory drug for too long a time, which may be a risk in case the animal does not tolerate the medicament.

The present invention solve the above problem by the use of the compound E-6087 in a weekly dosage which tries to maintain the comfort and advantages in adherence to treatment of a long-lasting action products but maintaining a sufficient margin of security.

E-6087 with formula:

was first disclosed in EP1083171 were its anti-inflammatory activity in rats was taught. However, this document is silent about any particular dosage regime in the treatment of degenerative joint disease.

BRIEF DESCRIPTION OF THE FIGURES

FIG. 2: represents the pain assessment in A) non-treated animals and B) in animals treated at day 0 and day 12 with 4 mg/kg of body weight of E-6087. Grey shadow represents the arthritis induction periods and black shadow represents the time (represented by the width of the black shadow) and pain score shown after each induction period. In non-treated animals pain reached half the highest score after each induction period. In the treated group although pain was not controlled after two hours of the first 4 mg/kg dose, it was slightly controlled on day 7 and totally controlled on days 14 and 21 after administration of a second 4 mg/kg dose on day 12.

After 10 weekly administrations of E-6087 (at steady-state), the 97% of treated dogs will reach levels higher than 536 ng/mL at $C_{max}$ ss. Based on these simulations results, this oral weekly dosing schedule seems to be adequate under a safety and efficacy point of view.

DETAILED DESCRIPTION OF THE INVENTION

The main object of the present invention is based in the discovery of a new dosage regime applicable to the treatment of pain and inflammation associated to degenerative joint diseases or conditions relying on the use of E-6087.

Actually, the object of the invention is compound E-6087 for use in the treatment of pain and inflammation associated to degenerative joint diseases or conditions in mammals comprising the administration of a maintenance weekly dosage regime from 1 to 6 mg/kg of body weight.

The weekly dosage regime presented in this invention has demonstrated to be effective in the treatment of pain and inflammation associated to degenerative joint diseases in an osteoarthritis induced model in dogs. The results shown in the examples demonstrate that a weekly dosage regime of E-6087 ranging from 1 to 6 mg/kg of body weight is capable of dramatically reducing lameness and pain around a week after the first dose administration and totally control lameness and pain from that moment on.

In addition to the maintenance weekly dosage regime hereby presented, an initial loading dose may be used in order to early achieve the desired effects of E-6087.

The loading dose or maintenance dose regime, if not otherwise specified, always refers to mg of product per kg of body weight (or mg/kg of body weight).

The weekly dosage regime means that the maintenance dose of E-6087 of 1 to 6 mg/kg of body weight must be administered on a 7 days basis so as to reach the desired effect. The more the administration is deferred from the established dosage regime, the less effective the treatment will be. Adhesion to the dosage regime is essential for the good results of the treatment. The weekly dosage regime as described in the present invention has nevertheless the advantage of combining a reasonable time between dose administrations, thus facilitating adhesion to treatment, with a reasonable margin of security.

The loading dose is an initial dose of 2 to 12 mg/kg of body weight which must be administered at the beginning of the treatment, namely on the first day of the treatment or if divided in two doses at preferably in the first and the second day of the treatment. The loading dose seeks early achievement of the desired effect and it use is specially suited for severe cases.

In the context of the invention, degenerative joint diseases are those diseases that result in the progressive loss of articular cartilage and subchondral bone. The causes of degenerative joint disease are varied and may include hereditary, developmental, metabolic and mechanical deficits. Symptoms may include joint pain, tenderness, stiffness, locking, and sometimes an effusion. Most commonly, degenerative joint disease is known as osteoarthritis although it may include other diseases including degenerative processes normally causing pain.

Degenerative joint conditions are understood in the present invention as situations or symptoms occurring in a subject suffering degenerative joint disease such as, for instance lameness in an animal suffering osteoarthritis in a leg.

The first aspect of the invention is compound E-6087 for use in the treatment of pain and inflammation associated to degenerative joint diseases or conditions, at a maintenance weekly dosage regime from 1 to 6 mg/kg of body weight.

In a particular embodiment of the invention, compound E-6087 is used for the treatment of pain and inflammation associated to degenerative joint diseases or conditions at a maintenance weekly dosage regime selected from 1.5 to 4.5 mg/kg of body weight.

In a still more particular embodiment, the maintenance weekly dosage regime is 4 mg/kg of body weight.

In another still more particular embodiment, the maintenance weekly dosage regime is 2 mg/kg of body weight.

In a particular and specially preferred embodiment the maintenance weekly dosage regime is preceded by an initial loading dose of E-6087.

The use of a loading dose of E-6087 preceding the maintenance weekly dosage regime is optimal for the severe cases or for treating acute to chronic pain/inflammation associated to degenerative joint diseases. The use of a loading dose allows for the early achievement of the desired effects of E-6087.

The loading dose may be administered in one time on the first day of treatment or divided into two doses, the first one being administered on the first day and the second one administered on the second day of treatment, or the first one and the second one being administered in different points in time of the same day. In any case, the loading dose is always administered at the beginning of the treatment and precedes the weekly dosage regime.

The loading dose of E-6087 is about 2 to 12 mg/kg of body weight, more preferably about 3,5 to 9 mg/kg.

In a particular and preferred embodiment, the maintenance dose regime of E-6087 is preceded by the administration of a loading dose of E-6087 of 8 mg/kg of body weight which is administered in one time at 8 mg/kg or twice at 4 mg/kg. When the loading dose is administered once, it must be administered in the first day of the treatment. When the loading dose is administered in two doses of 4 mg/kg, it may be administered at different points in time within the same starting day of the treatment. On the alternative, the first dose of 4 mg/kg may be administered once at the starting day of the treatment and the second one on the next day.

In this particular embodiment, the loading dose of E-6087 is preferably administered once at 8 mg/kg of body weight or if administered in two dose of 4 mg/kg of body weight, preferably the first dose is administered in the starting day of the treatment and the second one on the next day.

In the particular embodiment where a loading dose of E-6087 of 8 mg/kg of body weight is administered either in one time at 8 mg/kg or twice at 4 mg/kg, the treatment is followed by a weekly maintenance dosage of E-6087 of 4 mg/kg of body weight.

In another particular and preferred embodiment of the invention, the maintenance dose of E-6087 is preceded by administration of a loading dose of E-6087 of 4 mg/kg of body weight which is administered in one time at 4 mg/kg or twice at 2 mg/kg. When the loading dose is administered once, it must be administered in the first day of the treatment. When the loading dose is administered in two doses of 2 mg/kg, it may be administered at different points in time within the same starting day of the treatment. On the alternative, the first dose of 2 mg/kg may be administered once at the starting day of the treatment and the second one on the next day.

In this particular embodiment, the loading dose of E-6087 is preferably administered once at 4 mg/kg of body weight or if administered in two doses of 2 mg/kg of body weight, preferably the first dose is administered in the starting day of the treatment and the second one on the next day.

In the particular embodiment where a loading dose of E-6087 of 4 mg/kg of body weight is administered either in one time at 4 mg/kg or twice at 2 mg/kg, the treatment is followed by a weekly maintenance dosage of 2 mg/kg of body weight.

In a particular embodiment of the invention, compound E-6087 is used for the treatment of pain- and inflammation-associated to degenerative joint diseases or conditions wherein there is, additionally, an intitial loading dose.

As generally discussed above a particular and specially preferred embodiment of the invention is when compound E-6087 is used for the treatment of pain and inflammation associated to degenerative joint diseases or conditions wherein said use includes a(n initial) loading dose.

More particularly, compound E-6087 is used for the treatment of pain and inflammation associated to degenerative joint diseases or conditions at a loading dose selected from 2 to 12 mg/kg of body weight.

In a more particular and preferred embodiment, the loading dose of E-6087 is about 3,5 to 9 mg/kg of body weight.

In a specially preferred embodiment, the loading dose of E-6087 is about 8 mg/kg of body weight.

In a still more specially preferred embodiment, the loading dose of 8 mg/kg of body weight consists in one dose of 8 mg/kg or two doses of 4 mg/kg.

In another specially preferred embodiment, the loading dose of E-6087 is about 4 mg/kg of body weight.

In a still more specially preferred embodiment, the loading dose of 4 mg/kg of body weight consists in one dose of 4 mg/kg or two doses of 2 mg/kg.

A preferred embodiment of the invention is where the loading dose is 8 mg/kg of body weight and the weekly dosage regime is 4 mg/kg of body weight.

Another preferred embodiment of the invention is where the loading dose is 4 mg/kg of body weight and the weekly dosage regime is 2 mg/kg of body weight.

In a particular embodiment of the invention, compound E-6087 is used for the treatment of pain and inflammation associated to degenerative joint diseases or conditions in mammals following a treatment dosage regime as explained above, wherein the degenerative joint disease is osteoarthritis.

In another particular embodiment, compound E-6087 is used for the treatment of pain and inflammation associated to degenerative joint diseases or conditions in mammals following a treatment dosage regime as explained before, wherein the degenerative joint condition is lameness.

Although compound E-6087 can be used for the treatment of pain- and inflammation-associated to degenerative joint diseases or conditions to any kind of mammal following a treatment dosage regime as explained before, it is particularly useful for the treatment of dogs.

In another aspect the invention refers to method for the treatment of pain- and inflammation-associated to degenerative joint diseases or conditions in mammals comprising the administration of a maintenance weekly dosage regime of E-6087 from 1 to 6 mg/kg of body weight.

In a particular embodiment method for the treatment of the invention, comprises the administration of a maintenance weekly dosage regime selected of E-6087 from 1.5 to 4.5 mg/kg of body weight.

In a still more particular embodiment, the method of treatment comprises the administration of a maintenance weekly dosage regime of E-6087 of 4 mg/kg of body weight.

In another still more particular embodiment, the method of treatment comprises the administration of a maintenance weekly dosage regime of E-6087 of 2 mg/kg of body weight.

In a particular and specially preferred embodiment of the method of the invention, the maintenance weekly dosage regime is preceded by the administration of an initial loading dose of E-6087.

A loading dose of E-6087 preceding the weekly maintenance dose is optimal in the method of treatment for the severe cases or for treating acute to chronic pain/inflammation associated to degenerative joint diseases. A method of treatment comprising a loading dose allows the early achievement of the desired effects of E-6087.

The method of treatment of the invention may comprise a loading dose of E-6087 of about 2 to 12 mg/kg of body weight, more preferably of about 3,5 to 9 mg/kg.

In a particular and preferred embodiment, in the method of the invention the maintenance dose regime of E-6087 is preceded by the administration of a loading dose of E-6087 of 8 mg/kg of body weight which is administered in one time at 8 mg/kg or twice at 4 mg/kg. When the loading dose is administered once, it must be administered in the first day of the treatment. When the loading dose is administered in two doses of 4 mg/kg, it may be administered at different points in time within the same starting day of the treatment. On the alternative, the first dose of 4 mg/kg may be administered once at the starting day of the treatment and the second one on the next day.

In this particular embodiment of the method of the invention, the loading dose of E-6087 is preferably administered once at 8 mg/kg of body weight or if administered in two dose of 4 mg/kg of body weight, preferably the first dose is administered in the starting day of the treatment and the second one on the next day.

In the particular embodiment of the method where a loading dose of E-6087 of 8 mg/kg of body weight is administered either in one time at 8 mg/kg or twice at 4 mg/kg, the treatment is followed by a weekly maintenance dosage of E-6087 of 4 mg/kg of body weight.

In another particular and preferred embodiment of the method of the invention, the maintenance dose of E-6087 is preceded by administration of a loading dose of E-6087 of 4 mg/kg of body weight which is administered in one time at 4 mg/kg or twice at 2 mg/kg. When the loading dose is administered once, it must be administered in the first day of the treatment. When the loading dose is administered in two doses of 2 mg/kg, it may be administered at different points in time within the same starting day of the treatment. On the alternative, the first dose of 2 mg/kg may be administered once at the starting day of the treatment and the second one on the next day.

In this particular embodiment of the method, the loading dose of E-6087 is preferably administered once at 4 mg/kg of body weight or if administered in two dose of 2 mg/kg of body weight, preferably the first dose is administered in the starting day of the treatment and the second one on the next day.

In the particular embodiment of the method where a loading dose of E-6087 of 4 mg/kg of body weight is administered either in one time at 4 mg/kg or twice at 2 mg/kg, the treatment is followed by a weekly maintenance dosage of 2 mg/kg of body weight.

As generally discussed above the a particular and specially preferred embodiment of the invention is where the method of treatment comprises the administration of an intitial loading dose of compound E-6087.

In a preferred embodiment of the invention, the method of treatment of the invention comprises the administration of a loading dose of E-6087 of about 2 to 12 mg/kg of body weight.

In a still more particular and preferred embodiment, the method of treatment of the invention comprises the administration of a loading dose of E-6087 of about 3,5 to 9 mg/kg of body weight.

In a specially preferred embodiment, the method of treatment of the invention comprises the administration of a loading dose of E-6087 of about 8 mg/kg of body weight.

In another specially preferred embodiment, the method of treatment of the invention comprises the administration of a loading dose of E-6087 of about 4 mg/kg of body weight.

In a still more specially preferred embodiment, the method of treatment of the invention comprises the administration of a loading dose of E-6087 of about 8 mg/kg of body weight administered in one time 8 mg/kg or two times 4 mg/kg.

In another still more specially preferred embodiment, the method of treatment of the invention comprises the administration of a loading dose of E-6087 of about 4 mg/kg of body weight administered in one time 4 mg/kg or two times 2 mg/kg.

In a preferred embodiment of the invention, the method of treatment of the invention comprises the administration of a loading dose is 8 mg/kg of body weight and the weekly dosage regime is 4 mg/kg of body weight.

In another preferred embodiment, the method of treatment of the invention comprises the administration of a loading dose is 4 mg/kg of body weight and the weekly dosage regime is 2 mg/kg of body weight.

In another preferred embodiment of the method of treatment the loading dose is administered once on the first day of treatment.

In yet another preferred embodiment of the method of treatment the loading dose is administered in two doses at different points in time within the same starting day of treatment.

In a yet another preferred embodiment of the method of treatment the loading dose is administered in two doses, the first dose is administered once at the starting day of treatment and the second dose on the next day.

In a specially preferred embodiment of the method of treatment the loading dose of two times 4 mg/kg is administered at different points in time within the same starting day of treatment.

In another specially preferred embodiment of the method of treatment the loading dose of two times 2 mg/kg is administered at different points in time within the same starting day of treatment.

In a preferred embodiment, the loading dose is administered in two doses of 4 mg/kg, the first dose of 4 mg/kg is administered on the first day of treatment and the second dose on the next day.

In a particular embodiment of the method of the invention, compound E-6087 is administered for the treatment of pain and inflammation associated to degenerative joint diseases or conditions in mammals following a treatment dosage regime as explained above, wherein the degenerative joint disease is osteoarthritis.

In another particular embodiment of the method, compound E-6087 is administered for the treatment of pain and inflammation associated to degenerative joint diseases or conditions in mammals following a treatment dosage regime as explained before, wherein the degenerative joint condition is lameness.

Although a method for the treatment of pain- and inflammation-associated to degenerative joint diseases or conditions by administering compound E-6087 following a treatment dosage regime as explained before, is applicable top any kind of mammal it is particularly useful for the treatment of dogs.

A further aspect of the invention is the use of the compound E-6087 for the preparation of a medicament for the treatment of pain and inflammation associated to degenerative joint diseases or conditions, at a maintenance weekly dosage regime from 1 to 6 mg/kg of body weight.

In a particular embodiment of the invention, compound E-6087 is used for the preparation of a medicament for the treatment of pain and inflammation associated to degenerative joint diseases or conditions at a maintenance weekly dosage regime from 1.5 to 4.5 mg/kg of body weight.

In a still more particular embodiment, the maintenance weekly dosage regime is of 4 mg/kg of body weight.

In a still more particular embodiment, the maintenance weekly dosage regime is of 2 mg/kg of body weight.

In a particular and preferred embodiment of the invention, compound E-6087 is used for the preparation of a medicament for the treatment of pain and inflammation associated to degenerative joint diseases or conditions wherein there is, additionally, an intitial loading dose.

In a particular embodiment of the invention, compound E-6087 is used for the preparation of a medicament for the treatment of pain and inflammation associated to degenerative joint diseases or conditions wherein said use includes an initial loading dose.

In a particular and specially preferred embodiment compound E-6087 is used for the preparation of a medicament for the treatment of pain and inflammation associated to degenerative joint diseases or conditions at the maintenance weekly dosage regime and a loading dose of E-6087.

The use of a loading dose of E-6087 in the preparation of the medicament is optimal for the severe cases or for treating acute to chronic pain/inflammation associated to degenerative joint diseases. The use of a loading dose allows for the early achievement of the desired effects of E-6087.

In the use of E-6087 for preparing a medicament, the loading dose may be for one time administration on the first day of treatment or divided into two doses, the first one being administered on the first day and the second one administered on the second day of treatment, or the first one and the second one are administered in different points in time of the same day. In any case, the loading dose is always administered at the beginning of the treatment and precedes the weekly dosage regime.

In a particular and preferred embodiment, E-6087 is used in the preparation of a medicament where the maintenance dose regime of E-6087 is preceded by the administration of a loading dose of E-6087 of 8 mg/kg of body weight which is administered in one time at 8 mg/kg or twice at 4 mg/kg. When the loading dose is prepared to be administered once, it must be administered in the first day of the treatment. When the loading dose is prepared to be administered in two doses of 4 mg/kg, it may be administered at different points in time within the same starting day of the treatment. On the alternative, the first dose of 4 mg/kg may be prepared to be administered once at the starting day of the treatment and the second one on the next day.

In this particular embodiment, E-6087 is used for preparation of a medicament where the loading dose of E-6087 is preferably to be administered once at 8 mg/kg of body weight or if administered in two doses of 4 mg/kg of body weight, preferably the first dose is administered in the starting day of the treatment and the second one on the next day.

In the particular embodiment where E-6087 is used for preparation of a medicament with a loading dose of E-6087 of 8 mg/kg of body weight to be administered either in one time at 8 mg/kg or twice at 4 mg/kg, the treatment is followed by a weekly maintenance dosage of E-6087 of 4 mg/kg of body weight.

In another particular and preferred embodiment of the invention, E-6087 is used in the preparation of the medicament where the maintenance dose of E-6087 is preceded by a loading dose of E-6087 of 4 mg/kg of body weight which is administered in one time at 4 mg/kg or twice at 2 mg/kg. When the loading dose is prepared to be administered once, it must be administered in the first day of the treatment. When the loading dose is prepared to be administered in two doses of 2 mg/kg, it may be administered at different points in time within the same starting day of the treatment. On the alternative, the first dose of 2 mg/kg may be prepared to be administered once at the starting day of the treatment and the second one on the next day.

In this particular embodiment, E-6087 is used for preparation of a medicament where the loading dose of E-6087 is preferably to be administered once at 4 mg/kg of body weight or if administered in two doses of 2 mg/kg of body weight, preferably the first dose is administered in the starting day of the treatment and the second one on the next day.

In the particular embodiment where E-6087 is used for preparation of a medicament with a loading dose of E-6087 of 4 mg/kg of body weight to be administered either in one time at 4 mg/kg or twice at 2 mg/kg, the treatment is followed by a weekly maintenance dosage of 2 mg/kg of body weight.

In a particular embodiment of the invention, compound E-6087 is used for the preparation of a medicament for the treatment of pain and inflammation associated to degenerative joint diseases or conditions at a loading dose selected from 2 to 12 mg/kg of body weight.

In a still more particular and preferred embodiment, the loading dose of E-6087 used in the preparation of the medicament is about 3.5 to 9 mg/kg of body weight, In a specially preferred embodiment, the loading dose of E-6087 used in the preparation of the medicament is about 8 mg/kg of body weight.

In a still more specially preferred embodiment, the loading dose of 8 mg/kg of body weight consists in one dose of 8 mg/kg or two doses of 4 mg/kg.

In another specially preferred embodiment, the loading dose of E-6087 used in the preparation of the medicament is about 4 mg/kg of body weight.

In another still more specially preferred embodiment, the loading dose of 4 mg/kg of body weight consists in one dose of 4 mg/kg or two doses of 2 mg/kg.

In a preferred embodiment of the invention, E-6087 used in the preparation of the medicament where the loading dose is 8 mg/kg of body weight and the weekly dosage regime is 4 mg/kg of body weight.

In another preferred embodiment, E-6087 used in the preparation of the medicament where the loading dose is 4 mg/kg of body weight and the weekly dosage regime is 2 mg/kg of body weight.

In a particular embodiment of the invention, compound E-6087 is used for the preparation of a medicament for the treatment of pain and inflammation associated to degenerative joint diseases or conditions in mammals following a treatment dosage regime as explained above, wherein the degenerative joint disease is osteoarthritis.

In another particular embodiment, compound E-6087 is used for the preparation of a medicament for the treatment of pain and inflammation associated to degenerative joint diseases or conditions in mammals following a treatment dosage regime as explained before, wherein the degenerative joint condition is lameness.

Although compound E-6087 can be used for the preparation of a medicament for the treatment of pain and inflammation associated to degenerative joint diseases or conditions to any kind of mammal following a treatment dosage regime as explained before, it is particularly useful for the treatment of dogs.

A final object of the invention is represented by a composition comprising the compound E-6087 formulated for its administration in a maintenance weekly dosage regime from 1 to 6 mg/kg and at least one pharmaceutically acceptable excipient.

Another aspect of the invention is a composition comprising the compound E-6087 formulated for a maintenance weekly dosage regime from 1 to 6 mg/kg and at least one pharmaceutically acceptable excipient.

Another aspect of the invention is a composition comprising the compound E-6087 formulated as a medicament for a maintenance weekly dosage regime from 1 to 6 mg/kg and at least one pharmaceutically acceptable excipient.

Excipients can be selected among carriers, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of excipients and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral administration.

The composition of the invention can be formulated for oral administration in any form preferably selected from the group consisting of tablets, dragées, capsules, pills, chewing gums, powders, drops, gels, juices, syrups, solutions and suspensions.

The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

The composition according to the present invention may be produced according to standard procedures known to those skilled in the art.

Described below are a number of examples by way of illustration of the invention and do not limit it in anyway.

Experimental Models

Experimental Model 1: Acute Arthritis Induction in Dog

Two studies have been performed to evaluate the efficacy of E-6087 under different dosage regimes, by using a validated arthritis experimental model in dogs. In both studies, headed as examples 1 and 2, E-6087 was administered in its racemic form as pure powder.

The experimental model used in both studies was the same and it consists in the induction of an acute arthritis through the inoculation of an urate crystal suspension in the stifle (femorotibial) joint of dogs. In the negative control (untreated) dogs, this results in a transient inflammatory/painful reaction leading to a severe lameness detectable from 2 hours post-inoculation onwards and with a total duration of 8 to 10 hours, approximately. Partial or total inhibition of this reaction at a given time point after treatment administration is attributable to its pharmacological effect.

The protocol of this arthritis model is explained in the following paragraphs.

Protocol of the Reversible Urate Crystal Derived Arthritis Model used to Assess Antiinflamatory and Analgesic Effect The reversible urate crystal arthritis model used in next examples has been previously described in the literature [Toutain P. L. et al. J. Vet. Pharmacol. Therap. 24, 43-55, 2001].

A sodium urate crystal suspension at a concentration of 10 mg·mL-1 was prepared as follows:

Uric acid sodium salt (Sigma) was weighed in a 100 mL graduated flask.

0.9% NaCl solution was added to a final volume of 100 mL.

The suspension was mixed at room temperature by vortexing for approximately 5 min, by magnetic stirring for 5 min and was then sonicated for approximately 1 h.

The suspension was distributed in 1.5 mL vials and then autoclaved for 2 h at 120° C.

Finally the suspension was mixed by vortexing for 5 min, and sonicated for approximately 1 h.

The intra-articular injections were performed under general anaesthesia using Propovet multidose at a propofol dose of 6.5 mg.kg-1 by intravenous route without premedication. This induction medication was intended to result in a rapid onset anaesthesia with duration of about 10 minutes of unconsciousness and full recovery within approximately 30 minutes. For most of the dogs, Propovet multidose (half dose) was re-injected to maintain appropriate anaesthesia.

All urate crystal injections were introduced in the stifle (femorotibial) joint. The intra-articular injection was performed under aseptic conditions using a 30 mm long and 1 mm diameter sterile needle and a 2.5 mL syringe. The joint was checked for successful joint puncture, by synovial aspiration. One millilitre of urate crystal suspension was used for each intra-articular injection.

The duration of the induced inflammatory process was expected to be approximately 16 to 24 h and the average time of maximum lameness in untreated animals 2 to 3 hours after induction.

To assess the anti-inflammatory and analgesic effect of the test item, two clinical signs of arthritis were investigated: lameness and pain, respectively. Their intensity was determined using the following scoring systems:

| LAMENESS SCORE | Score |
| --- | --- |
| NO lameness - Full weight bearing | 0 |
| MODERATE lameness - Partial weight bearing | 1 |
| SEVERE lameness - No weight bearing to toe touching | 2 |

| PAIN SCORE | Score |
| --- | --- |
| No sign of pain during palpation | 0 |
| Signs of mild pain (eg turned head in recognition) | 1 |
| Signs of moderate pain (eg pulled limb away) | 2 |
| Signs of severe pain (eg vocalized or became aggressive) | 3 |
| Did not allow limb palpation | 4 |

Experimental Model 2: Dogs with Naturally Acquired Osteoarthritis

One study (headed as example 3) has been performed to evaluate the efficacy of E-6087 in dogs with naturally occurring osteoarthritis under real field conditions. E-6087 was administered in tablets.

For a dog to be included in the study, the following criteria must be fulfilled:

1. Owner's consent obtained prior to the start of any study activities.
2. Age ≥12 months.
3. Body weight ≥5 kg.
4. Clinical signs of osteoarthritis for one (with the exception of the spine including spinal joints, cranium, and vertebral column) or more joints for at least 3 weeks.
5. Confirmation by radiographic evidence of the presence of osteoarthritis in the dog. If radiographic evidence of the presence of osteoarthritis in the dog was not available, the dog had an X-ray (or equivalent e.g. scan) taken prior to enrolment to show evidence of osteoarthritis of the affected joint(s).
6. Minimum Clinical Sum Score (CSS) ≥6. If more than one joint was affected by OA, the most severely affected joint (with the exception of the spine) was assessed subsequently for efficacy.

Once included, dogs were randomly assigned to a treatment group. A practitioner was in charge of administering either a Placebo or E-6087 under two different dosage regimes to animals, while another one was in charge of blindly evaluating the progression of clinical signs during a 42-day follow-up.

A Clinical Sum Score (CSS) was used for the assessment of pain and lameness at several time points during the follow-up, including clinical assessments in this order for posture, lameness at walk, lameness at rot and pain at palpation/manipulation. The CSS was the sum of the individual scores.

| | Score |
| --- | --- |
| POSTURE (DOG STANDING) | |
| Normal stance | 0 |
| Slightly abnormal stance: partial weight bearing of limbs but paw remains firmly in contact with floor | 1 |
| Markedly abnormal stance: partial weight bearing of limb with minimal contact between paw and the floor | 2 |
| Severely abnormal stance: no weight bearing | 3 |
| LAMENESS AT WALK | |
| No lameness: normal weight bearing on all limbs | 0 |
| Mild lameness with partial weight bearing | 2 |
| Obvious lameness with partial weight bearing | 4 |
| Marked lameness with no weight bearing | 6 |
| LAMENESS AT TROT | |
| No lameness: normal weight bearing on all limbs | 0 |
| Mild lameness with partial weight bearing | 2 |
| Obvious lameness with partial weight bearing | 4 |
| Marked lameness with no weight bearing | 6 |
| PAIN ON PALPATION/MANIPULATION | |
| No pain on palpation/manipulation of affected joint | 0 |
| Mild pain (e.g. turns head in recognition) | 1 |
| Moderate pain (e.g. pulls limb away) | 2 |
| Severe pain (e.g. vocalizes or becomes aggressive or will not allow Investigators to palpate/manipulate the joint due to pain) | 3 |

EXAMPLES

Example 1

Efficacy Assessment of Oral Administration of E-6087 Following an Acute Arthritis Induction in Dog This study was designed to determine whether the blood levels of E-6087 achieved after one single oral dose of E-6087 at 4 mg/kg in dog, do have some short and/or long-term antiinflammatory and analgesic effects. In addition, a second dose of E-6087 at 4 mg/kg was administered to evaluate the eventual effect derived from the accumulation of the molecule in blood. The study had a total duration of 28 days.

The study was performed with seven male Beagle dogs randomly allocated to 3 groups. Dogs in the Control group did not received any treatment while dogs in the Treated groups received E-6087 at 4 mg/kg on days D0 and D12:

| Treatment Regimen | Groups I and II (n = 3 dog each) | Group III (Control Group) (n = 1 dog) |
| --- | --- | --- |
| 1$^{st}$ dose | E-6087 p.o. at 4 mg/kg (Day 0) | — |
| 2$^{nd}$ dose | E-6087 p.o. at 4 mg/kg (Day 12) | — |

During the study, the arthritis induction model was implemented on four occasions to each dog:
In dogs of Group I, on Days 0*, 7, 14** and 21.
In dogs of Group II, on Days 2, 7, 14 and 21.
In dogs of Group III, on Days 0, 14 and 28.
* two hours after product administration
** 48 hours after E-6087 administration, significant blood levels of E-6087 are achieved.

According to the institutional ethics committee's recommendations, the first and third inoculations were done in the right stifle while the second and fourth inoculations were done in the left stifle. On each day of arthritis induction, the anti-inflammatory and analgesic efficacy of treatments was assessed at different time points (just before the inoculation, and 0.5, 1, 2, 3, 4, 6, 9 and 12 hours later). Two clinical signs of arthritis were assessed by using a scoring system at each time point: visual lameness (whilst standing and walking) and pain at (inoculated stifle) palpation. The median, minimal and maximal values for this parameter were determined for each group at each time point. Blood sampling was performed at different time points during the study in dogs of groups I and II in order to determine blood concentrations of E-6087.

Figure 1A:
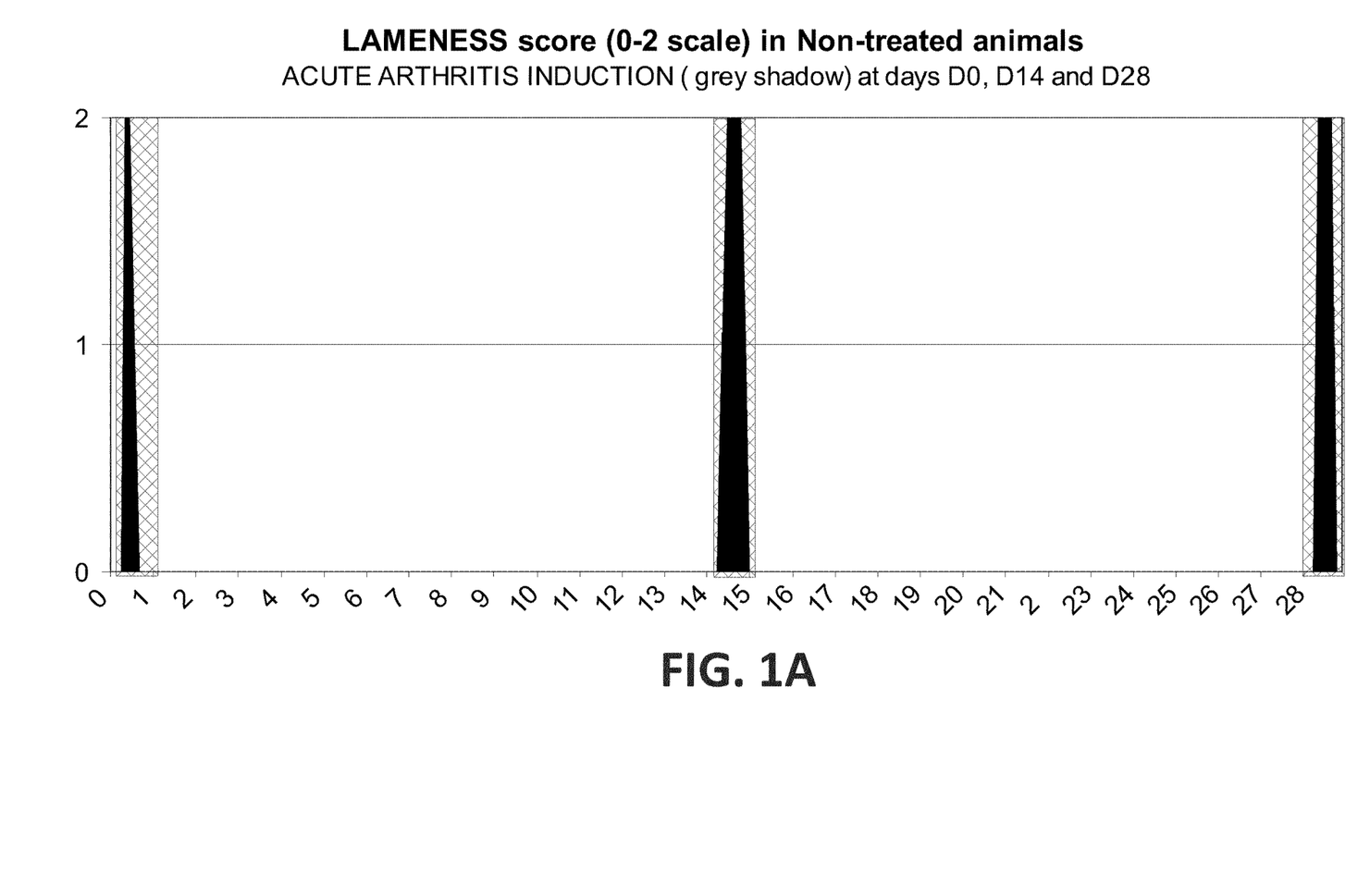
FIG. 1: represents the lameness assessment in A) non-treated animals and in B) animals treated at day 0 and day 12 with 4 mg/kg of body weight of E-6087. Grey shadow represents the arthritis induction periods and black shadow represents the time (represented by the width of the black shadow) and score of lameness shown after each induction. Non-treated animals show the highest lameness score after each induction period. In the treated group, although lameness was not controlled two hours after the first 4 mg/kg dose of E-6087 it was slightly controlled on day 7 of treatment and totally controlled on days 14 and 21 after administration of a second 4 mg/kg dose on day 12.
Figure 1B:
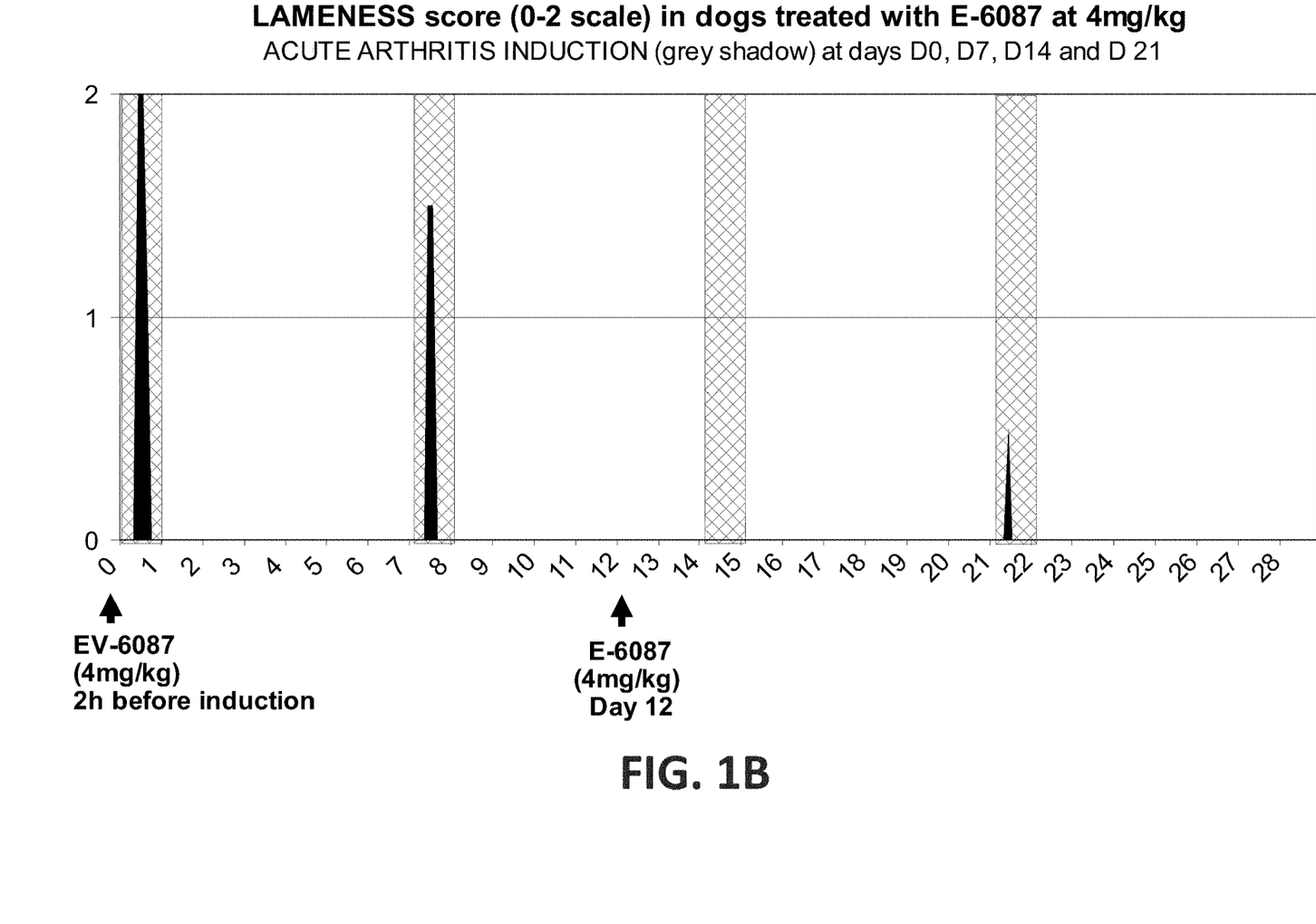

Results:

Lameness assessment: FIG. 1 shows the results in the lameness assessment. In the Control group, lameness reached the highest score after each induction. However, in the Treated group, although two hours after the first 4 mg/kg dose of E-6087 lameness was not controlled at all, it was slightly controlled on day D7 and absolutely controlled after the second 4 mg/kg dose of E-6087 (D14 and D21).

Figure 2A:
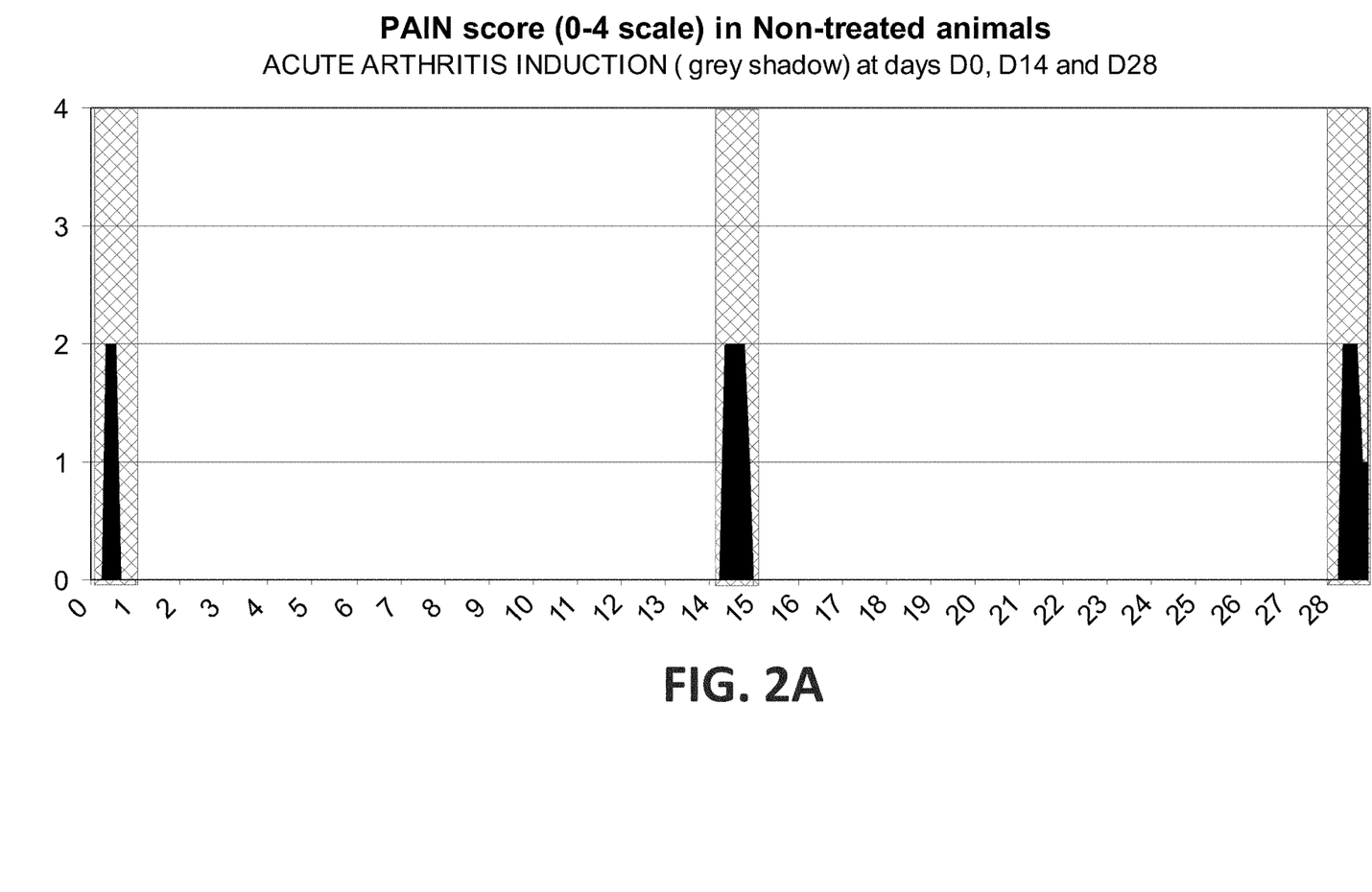
Figure 2B:
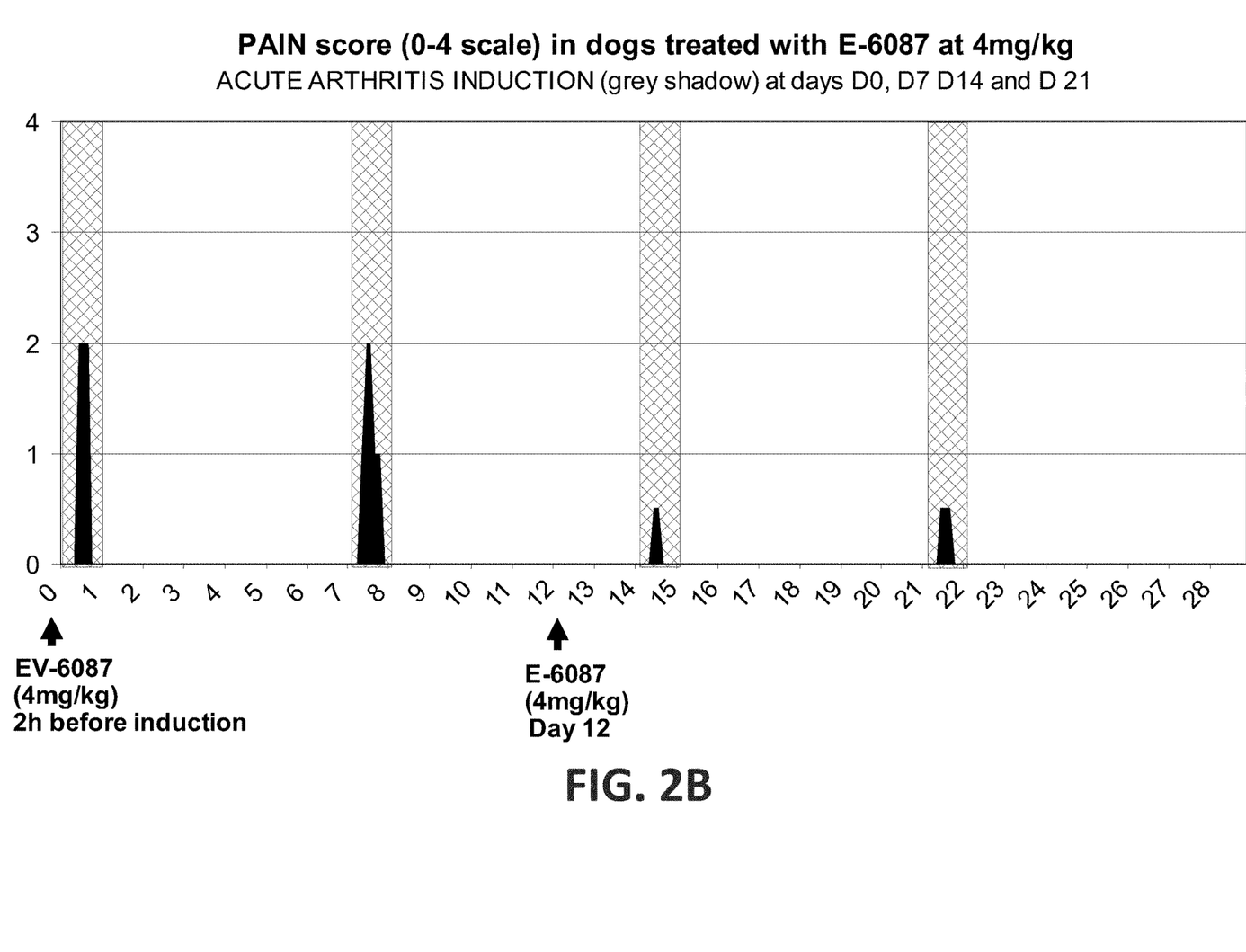

Pain assessment: FIG. 2 shows the results in the pain assessment. In the Control group, pain reached half the highest score after each induction. However, in the Treated group, although two hours after the first 4 mg/kg dose of E-6087 pain was not controlled at all, it was slightly controlled on day D7 and absolutely controlled after the second 4 mg/kg dose of E-6087 (D14 and D21).

These results indicate that cumulative blood concentrations of E-6087 achieved after the second dose of 4 mg/kg (administered 12 days after the first dose) lead to a rapid anti-inflammatory/analgesic effect that persisted at least during nine days. The ulterior analysis of blood samples from dogs treated with E-6087 confirmed an increase in plasma levels after the administration of the second dose of compound.

No adverse reactions related to the E-6087 administration were observed throughout the study.

Conclusions:

The results obtained in this study leads to the overall conclusion that:

two doses of 4 mg/kg of E-6087 in approximately less than twelve days are necessary to achieve clinically effective E-6087 blood concentrations.

Repeated administrations of E-6087 at 4 mg/kg, in approximately less than twelve days, progressively helps dogs to control experimentally induced lameness and pain. Consequently, it can be considered as a useful treatment for chronic conditions needing long-lasting therapy.

Example 2

Efficacy Assessment of an Oral Administration of a Loading Dose and Maintaining Doses of E-6087 Following an Acute Arthritis Induction in Dogs This study was designed to evaluate the effectiveness of two different treatment regimes for E-6087. In both cases it was administered a loading dose, followed by a weekly maintenance dose.

The study was performed with 13 male Beagle dogs from 13 to 35 months old and weighing from 9.45 and 13.02 kg, randomly allocated to 4 groups:

| Study day | Groups A and B (n = 4 dogs each) Treatment regimen I | | Group C (n = 4 dogs) Treatment regimen II | Group D (n = 1 dog) Control Group |
|---|---|---|---|---|
| Day 0 | EV-6087 p.o. at 4 mg/kg | Loading dose | EV-6087 p.o. at 8 mg/kg | — |
| Day 1 | EV-6087 p.o. at 4 mg/kg | | — | — |
| Day 7 | EV-6087 p.o. at 4 mg/kg | Maintenance dose | EV-6087 p.o. at 4 mg/kg | — |
| Day 14 | EV-6087 p.o. at 4 mg/kg | | EV-6087 p.o. at 4 mg/kg | — |
| Day 21 | EV-6087 p.o. at 4 mg/kg | | EV-6087 p.o. at 4 mg/kg | — |

During the study, the arthritis induction model was implemented on three occasions to each dog:

In dogs of Group A: on Day 2, Day 9 and Day 23.

In dogs of Group B: on Day 4, Day 14 (before treatment) and Day 28.

In dogs of Group C: on Day 0 (2 hours after treatment), Day 9 and Day 21 (before treatment).

In dogs of Group D: on Day 0, Day 14 and Day 28.

According to the institutional ethics committee's recommendations, the first and third inoculations were performed in the right stifle while the second inoculation was performed in the left stifle. On each day of arthritis induction, the anti-inflammatory and analgesic efficacy of treatments was assessed at different time points (just before the inoculation, and 0.5, 1, 2, 3, 4, 6, 9 and 12 hours later).

Two clinical signs of arthritis were assessed by using a scoring system at each time point: visual lameness (whilst standing and walking) and pain at (inoculated stifle) palpation. A combined visual lameness score, determined as the sum of the standing and walking lameness scores, was calculated and finally used for efficacy evaluation. The median, minimal and maximal values for this parameter were determined for each group at each time point.

Blood sampling was performed at different time points during the study in dogs of groups A, B and C in order to determine blood concentrations of E-6087 and to relate it with the observed pharmacological effect.

Figure 3:
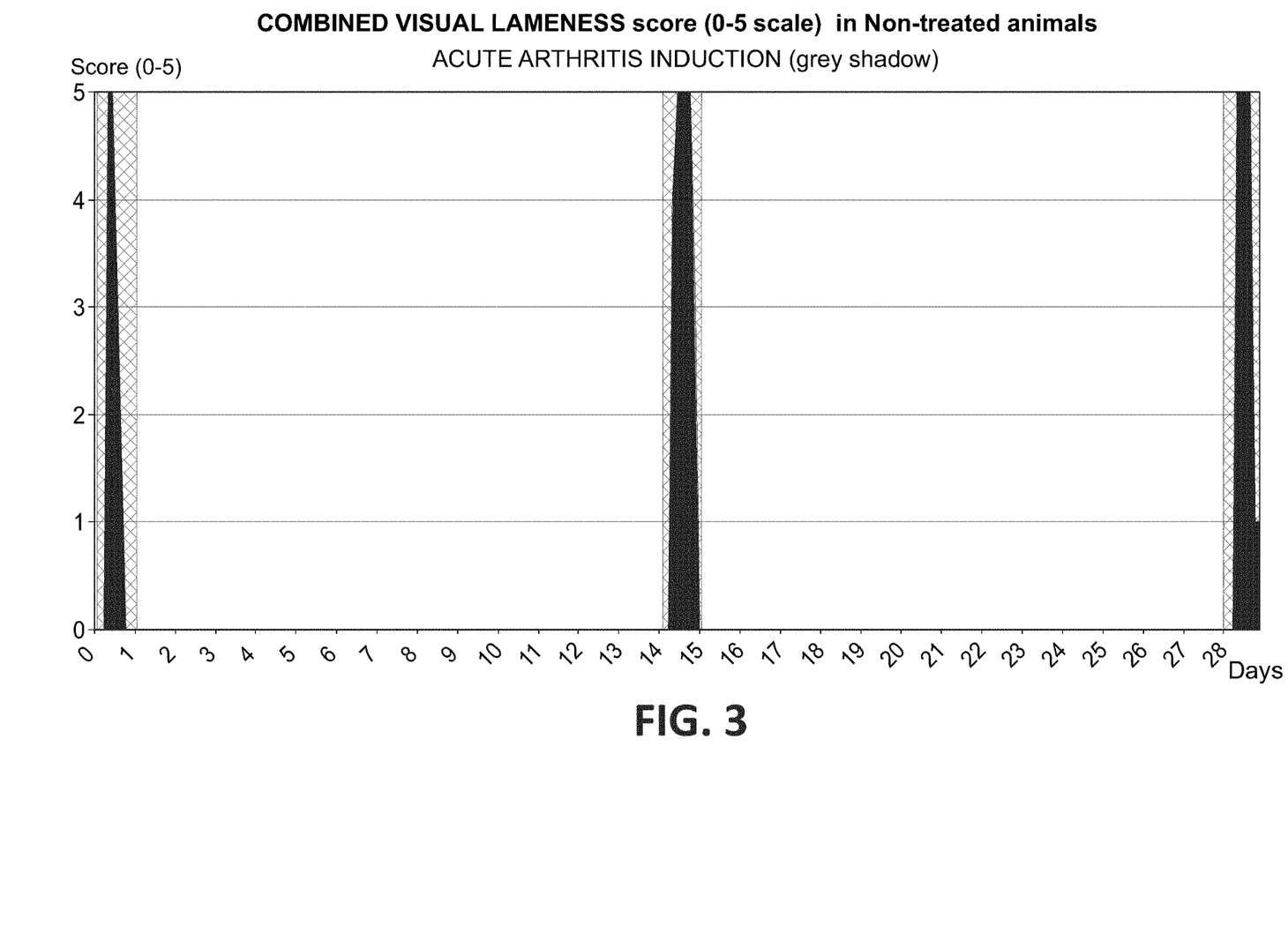
FIG. 3: represents the combined visual lameness assessment in non-treated animals showing the highest lameness score after each induction period (Days 0, 14 and 28)

Results:

A severe inflammatory/painful reaction was observed after the arthritis induction on Days 0, 14 and 28 in the untreated group (Group D), this confirming the validity of the arthritis experimental model used (FIG. 3)

In dogs of Groups A and B (treatment regimen I), mild inflammatory/painful reactions were observed after the arthritis inductions implemented during the first two weeks (Days 2, 4 and 9), and none (or very mild) reactions were observed after inductions performed on Days 14, 23 and 28. This indicates that blood concentrations of E-6087 achieved after the loading dose in this group (4 mg/kg on Days 0 and 1) were sufficient to achieve an anti-inflammatory effect, while continuing the treatment regimen with 4 mg/kg weekly maintenance doses, sufficient blood levels of E-6087 were rapidly achieved, therefore inhibiting the lameness associated to the experimentally induced arthritis.

On the other hand, in dogs of Group C (treatment regimen II), although a severe inflammatory/painful reaction was observed after the arthritis induction implemented on Day 0 (two hours after the 8 mg/kg loading dose), a very mild reaction was observed from Day 9 onwards, while continuing the treatment regimen with the 4 mg/kg weekly maintenance doses. At Day 9 this reaction was lower to that observed in Group A on the same time point. Consequently, the efficacy of E-6087 seemed to appear earlier when implementing the treatment regimen II (single loading dose of 8 mg/kg).

Figure 4:
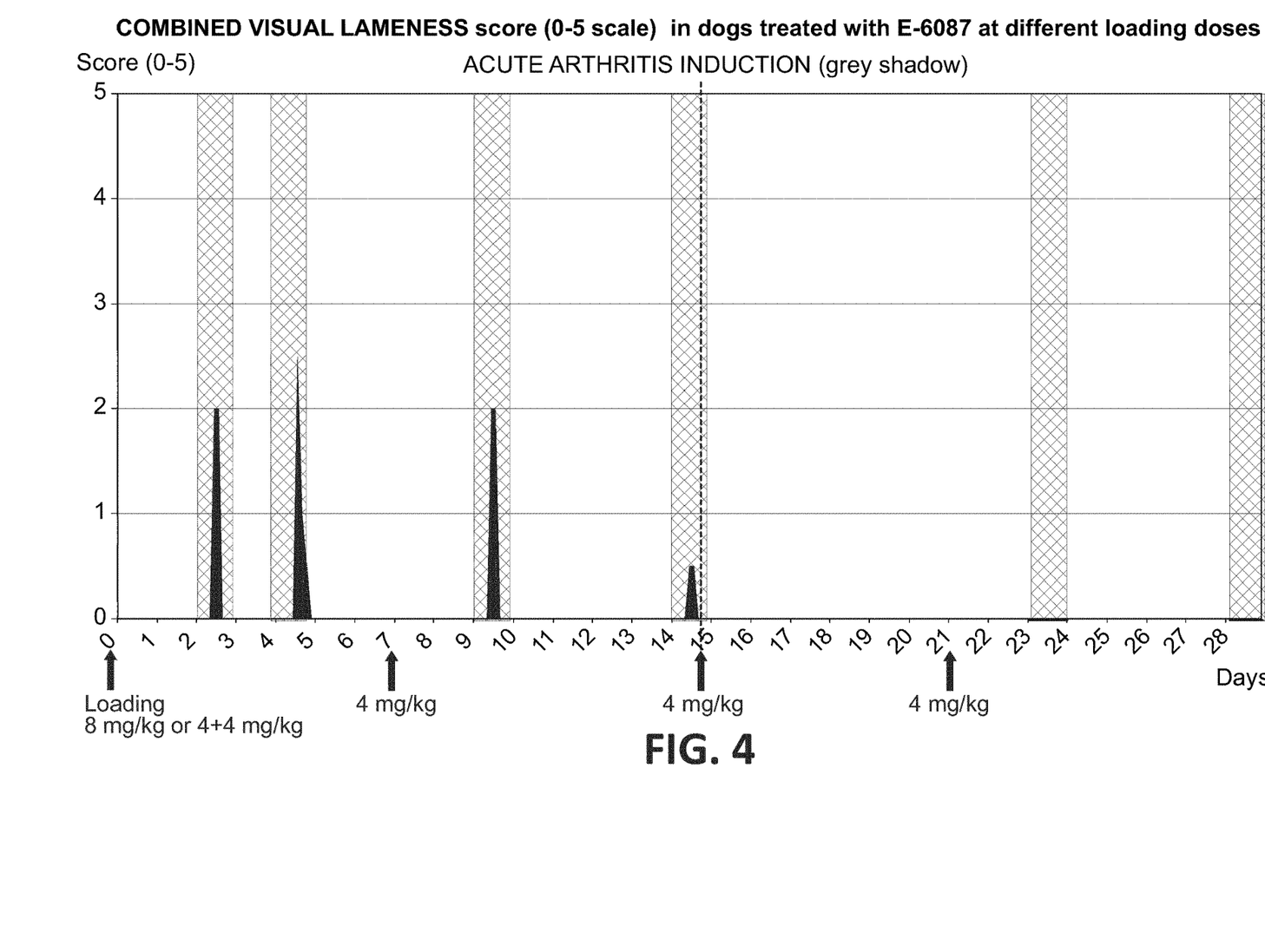
FIG. 4: represents the overall results referring to the combined visual lameness assessment in animals from groups A, B and C after induction on Days 2, 4, 9, 14, 23 and 28. The results evidence the progressive anti-inlfammatory/analgesic effect of repeated administration of E-6087.

The overall results of groups A, B and C evidencing the progressive anti-inflammatory/analgesic effect of repeated administration of E-6087 are summarized in FIG. 4.

Figure 5:
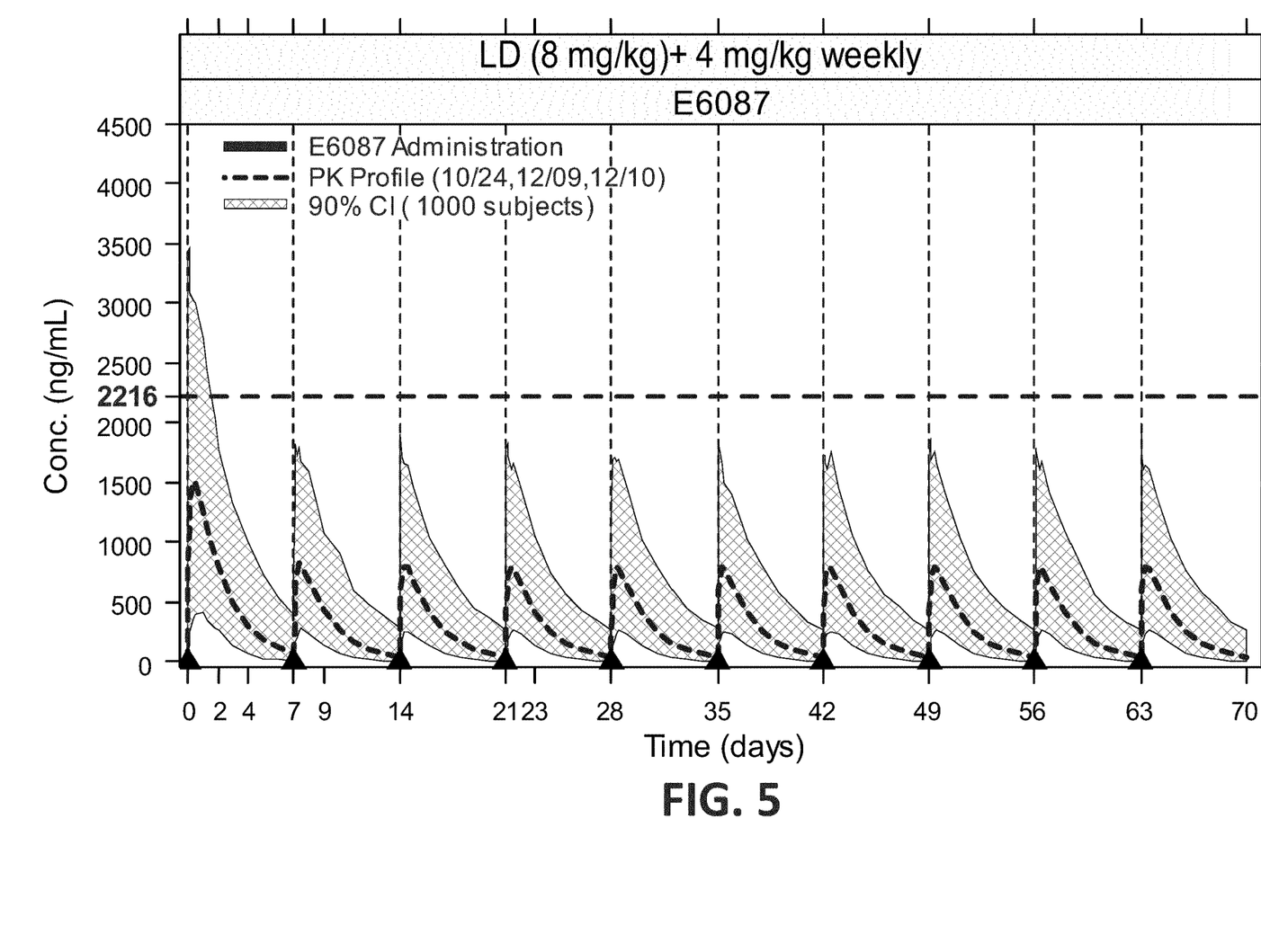
FIG. 5: Scatter plot of typical pharmacokinetic profile along with the 90% confidence intervals from simulated data after administration of loading dose of 8 mg/kg followed by 4 mg/kg weekly of E-6087. Only 15% of animals will achieve E-6087 levels higher than 2216 ng/mL (Minimum toxic concentration—MTC- for E-6087) during few hours after the first drug administration. For the subsequent weekly doses, it is not expected that any animal reaches drug levels higher than MTC for E-6087.
Figure 6:
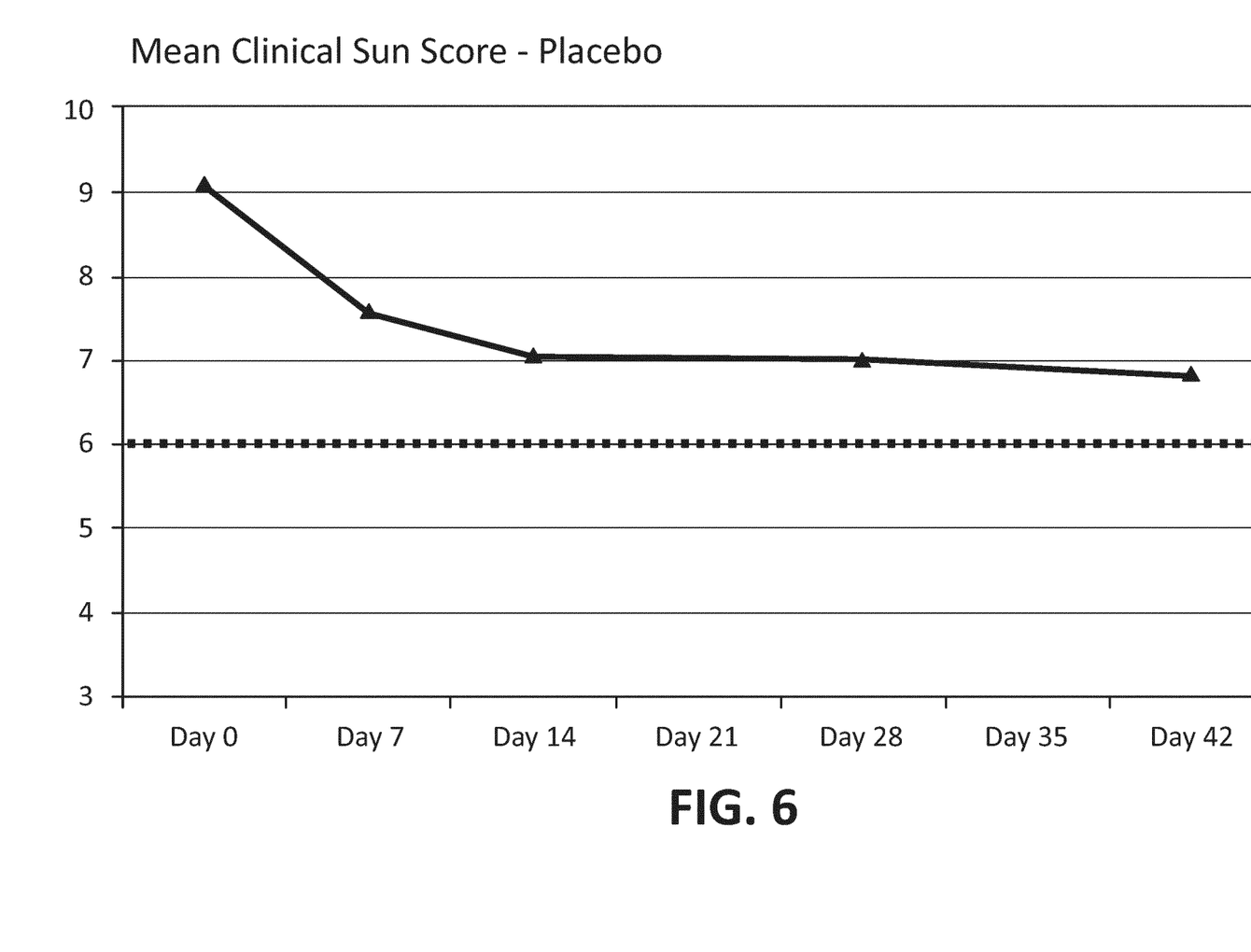
FIG. 6: represents the progression of the mean 'Clinical Sum Scores' (CSS) over time in dogs with naturally occurring osteoarthritis treated with a placebo in a randomized, blinded multi-centre clinical trial performed under real field conditions. A CSS below 6 (dashed line) was required for considering the improvement as clinically relevant.
Figure 7:
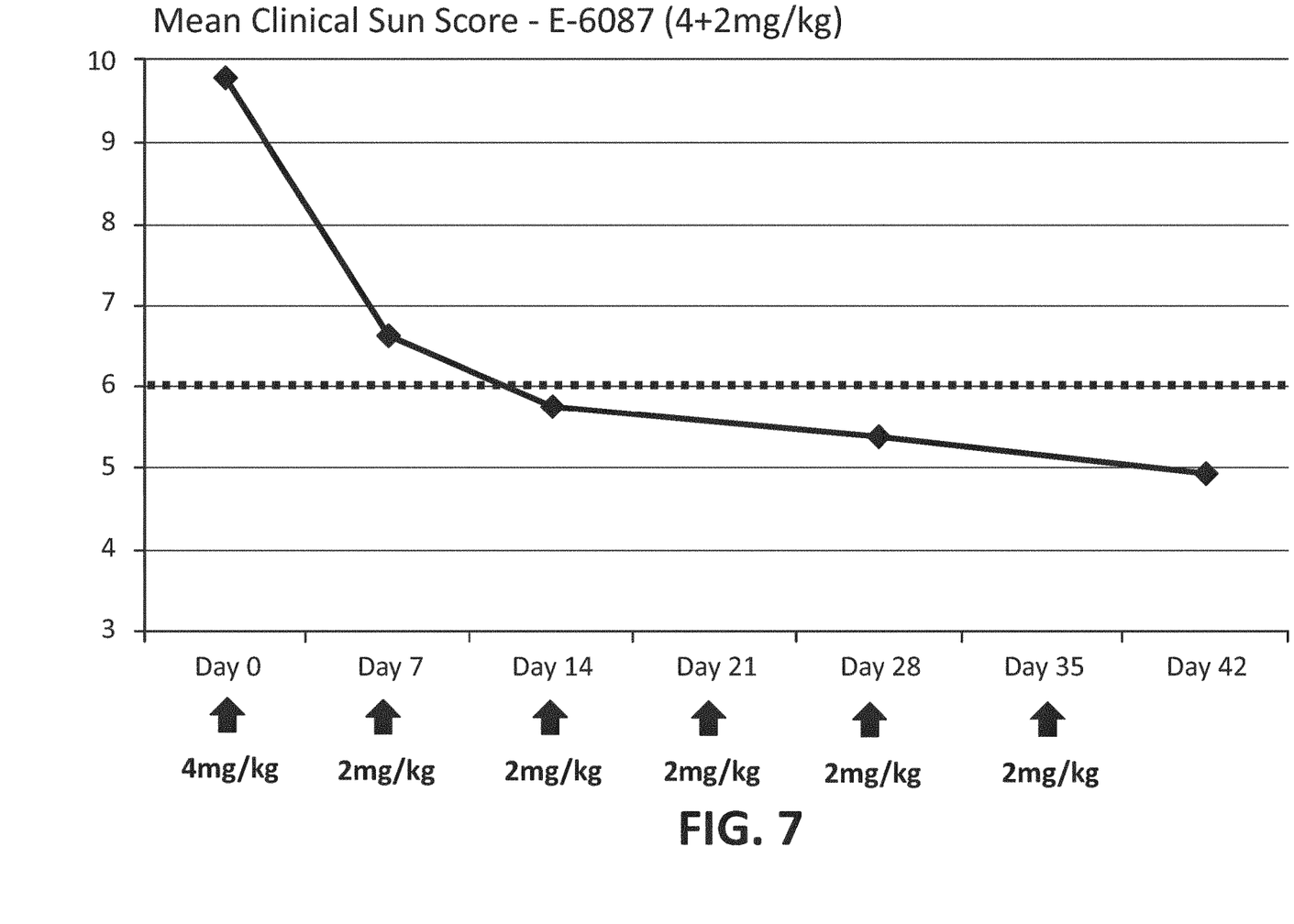
FIG. 7: represents the progression of the mean 'Clinical Sum Scores' (CSS) over time in dogs with naturally occurring osteoarthritis treated with a loading dose of 4 mg/kg followed by 2 mg/kg weekly of E-6087 in a randomized, blinded multi-centre clinical trial performed under real field conditions. A CSS below 6 (dashed line) was required for considering the improvement as clinically relevant.

Conclusions:

It was concluded that a treatment regimen of 4 mg/kg once weekly may be sufficient for mild cases or for treating chronic pain/inflammation The most suitable treatment regimen for more severe cases or for treating acute to chronic pain/inflammation using E-6087 was a single loading dose of 8 mg/kg or two consecutive loading doses of 4 mg/kg followed by several maintenance doses of 4 mg/kg, respectively. The use of a loading dose may also be optimal to achieve early the desired effect of the medicament. FIG. 5 depicts the typical pharmacokinetic profile of E-6087 with the associated variability (90% confidence intervals) after administration of a loading dose of 8 mg/kg followed by maintenance dose of 4 mg/kg weekly of 6087 in dogs.

No adverse reactions related to the E-6087 administration were observed throughout the study in Groups A, B and C.

Example 3

Efficacy Assessment of E-6087 Administered at a Loading Dose of 4 mg/kg Followed by Weekly Maintenance Doses of 2 mg/kg in Dogs with Naturally Occurring Osteoarthritis This study was designed to evaluate the effectiveness of E-6087 under real field conditions. E-6087 was administered at a loading dose of 4 mg/kg followed by weekly maintenance doses of 2 mg/kg The study was designed as a controlled, randomized, blinded, multi-centre clinical trial.

A total of 60 osteoarthritic dogs were included in the E-6087 group and 60 dogs in the Placebo group. All dogs underwent a follow-up period of 42 days, with clinical evaluations of lameness and pain on days 0, 7, 14, 28 and 42. A Clinical Sum Score (CSS) was calculated for the lameness and pain parameters at each time point.

In order to be enrolled in the study all dogs must had a Clinical Sum Score (CSS) of 6 or >6 on day 0.

Results:

The results showed that dogs in the Placebo group experienced a progressive reduction in CSS thorough the follow-up period. However, mean CSS in this group remain above the threshold of 6, meaning that reduction of lameness and pain was not clinically relevant.

On the other hand, dogs treated with E-6087 experienced a more marked reduction in CSS from day 0 onwards, being this reduction statistically significant by day 28 (P<0.05) and highly significant by day 42 (P<0.01), when compared to the Placebo group. According to the results, mean CSS in the treated group dropped under the threshold of 6 between day 7 and day 14, meaning that reduction of lameness and pain become clinically relevant shortly after the start of treatment.

Conclusions:

It was concluded that a treatment regimen of 2 mg/kg of EV-6087 once weekly after a loading dose of 4 mg/kg may be sufficient for reducing acute and/or chronic pain/inflammation in animals with naturally occurring osteoarthritis. The use of a loading dose may also be optimal to achieve early the desired effect of the medicament.

The invention claimed is:

1. A method for treating pain and/or inflammation associated with degenerative joint diseases or conditions in a dog, the method comprising administering to the dog an initial loading dose of a first composition comprising compound E-6087 of about 8 mg/kg of body weight of the dog as a single dose or as two doses of 4 mg/kg each separated by one day, and thereafter administering to the dog once weekly maintenance doses of a second composition comprising compound E-6087 of from 1 to 6 mg/kg of body weight of the dog.

2. The method of claim 1, wherein the once weekly maintenance doses are from 1.5 to 4.5 mg/kg of body weight of the dog.

3. The method of claim 1, wherein the initial loading dose is 8 mg/kg of body weight of the dog and the once weekly maintenance doses are each 4 mg/kg of body weight of the dog.

4. The method of claim 1, wherein the once weekly maintenance doses are each 2 mg/kg of body weight of the dog.

5. The method of claim 1, wherein the degenerative joint disease or condition is an arthritis-related disease or condition.

6. The method of claim 5, wherein the arthritis-related disease or condition is osteoarthritis or arthritis-related lameness.

7. The method of claim 1, wherein the pain and/or inflammation associated with degenerative joint diseases or conditions in the dog pain is chronic pain and/or inflammation.

8. The method of claim 1, wherein the pain and/or inflammation associated with degenerative joint diseases or conditions in the dog pain is acute pain and/or inflammation.

* * * * *

UNITED STATES PATENT AND TRADEMARK OFFICE
CERTIFICATE OF CORRECTION

PATENT NO. : 11,154,536 B2
APPLICATION NO. : 15/518871
DATED : October 26, 2021
INVENTOR(S) : Homedes-Beguer et al.

It is certified that error appears in the above-identified patent and that said Letters Patent is hereby corrected as shown below:

On the Title Page

Item (57) Abstract, Line 1, please replace --compounds-- with --compound--.

In the Drawings

Figure 1B, lower left, please replace --EV-6087-- with --E-6087--.
Figure 2B, lower left, please replace --EV-6087-- with --E-6087--.

In the Specification

Column 2, Lines 54-55, please replace --prescripting-- with --prescribing--.
Column 2, Line 66, please replace --products-- with --product--.
Column 6, Line 21, please replace --intitial-- with --initial--.
Column 6, Line 26, please replace --a(n initial)-- with --an initial--.
Column 8, Line 6, please replace --the a particular-- with --the particular--.
Column 11, Line 19, please replace --associated to-- with --associated with--.
Column 11, Line 20, please replace --conditions to-- with --conditions of--.
Column 17, Line 34, please replace --2 mg/kg-- with --2 mg/kg.--

Signed and Sealed this
Twenty-fifth Day of October, 2022

Katherine Kelly Vidal
*Director of the United States Patent and Trademark Office*